United States Patent [19]
Aller et al.

[11] 4,251,523
[45] Feb. 17, 1981

[54] SAFENED PHOSPHOROTHIOLATE PESTICIDAL COMPOSITIONS

[75] Inventors: Harold E. Aller, Norristown; Carl O. Hansen, Fort Washington, both of Pa.

[73] Assignee: Rohm and Haas Company, Philadelphia, Pa.

[21] Appl. No.: 12,271

[22] Filed: Feb. 15, 1979

Related U.S. Application Data

[63] Continuation of Ser. No. 594,132, Jul. 7, 1975, abandoned.

[51] Int. Cl.$^3$ .................. A01N 57/00; A01N 29/04
[52] U.S. Cl. .................................. 424/225; 424/352; 424/354
[58] Field of Search .................. 424/225, 352, 354

[56] References Cited

U.S. PATENT DOCUMENTS

| 3,824,306 | 7/1974 | Tsuchiya et al. | 424/219 |
| 3,839,511 | 10/1974 | Kishino et al. | 260/964 |
| 3,894,149 | 7/1975 | Mast | 424/352 |

Primary Examiner—Leonard Schenkman
Attorney, Agent, or Firm—Bernard J. Burns

[57] ABSTRACT

Insecticidal compositions which comprise an O-ethyl S-n-propyl O-halophenyl phosphorothiolate can be safened by adding to the compositions a safening amount of toxaphene (octochlorocamphene) or DDT. These safened compositions are particularly useful in controlling insects in growing cotton crops.

6 Claims, No Drawings

SAFENED PHOSPHOROTHIOLATE PESTICIDAL COMPOSITIONS

The Disclosure

This invention relates to safened insecticidal compositions which comprise an O-ethyl S-n-propyl O-halophenyl phosphorothiolate and which comprise toxaphene or DDT as a safening agent, and to methods of controlling insects with these compositions.

The use of insecticides in controlling insects in agronomic crops has become a standard worldwide agricultural practice. However, many compounds which have significant insecticidal activity also cause severe injury to many important crops. Consequently, although the compound will successfully control the insects in the crops, the high degree of phytotoxicity caused by the compounds eliminates the possibility of commercial use of the compound on that crop.

It has now been found that insecticidal compositions which comprise an O-ethyl S-n-propyl O-halophenyl phosphorothiolate can be safened so as to limit undesirable phytotoxicity by adding to these compositions a safening amount of toxaphene (octachlorocamphene) or DDt (2,2-bis(4-chlorophenyl)-1,1,1-trichloroethane). Generally, in the safened insecticidal compositions of the invention the phosphorothiolate and the toxaphene or DDT will be combined in a weight ratio (phosphorothiolate:safening agent) of about 2:1 to about 1:10, and preferably about 1:1 to about 1:5. When DDT is used as a safening agent, the most preferred ratio is about 1:2 to 1:5. Mixtures of toxaphene and DDT can also be used as the safening agent.

The phosphorothiolates which can be used in the compositions of the invention have the formula

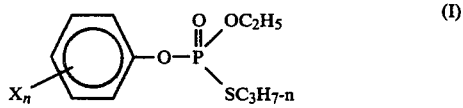

wherein

X is a halogen atom preferably bromine or chlorine, and n is 1, 2 or 3.

The preferred phosphorothiolates in the compositions of the invention are O-ethyl S-n-propyl O-2,4,6-trichlorophenyl phosphorothiolate and O-ethyl S-n-propyl O-4-bromo-2-chlorophenyl phosphorothiolate.

The compositions of the invention are useful for controlling insects in a wide variety of crops, including cotton, soybeans, wheat, corn, and the like. However, the compositions are especially useful in cotton. The phosphorothiolate when used alone severly injures the cotton plants. However, when toxaphene or DDT is added to the compositions, little or no phytotoxicity is observed. The compositions of the invention are usually applied to the crop at a rate of about 0.5 to about 12 pounds of active ingredient (total phosphorothiolate plus safening agent) per acre, and preferably from about 0.75 to about 5 pounds of active ingredient per acre.

The compositions of the invention are generally applied to the crop to be treated in an agricultural formulation which also comprises an agronomically acceptable carrier. By agronomically acceptable carrier is meant any substance which can be used to dissolve, disperse, or diffuse an active compound in the composition without impairing the effectiveness of the compound and which by itself has no detrimental effect on the soil, equipment, crops, or agronomic environment. The compositions of the invention can be either solid or liquid formulations or solutions. For example, the compounds can be formulated as wettable powders, emulsifiable concentrates, and dusts. In such formulations, the compounds are extended with a liquid or solid carrier and, when desired, suitable surfactants are incorporated.

It is usually desirable to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

For the preparation of emulsifiable concentrates, the active compounds can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent, soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product.

Wettable powders suitable for spraying, can be prepared by admixing the active compounds with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to about 60% by weight. A dispersing agent can constitute about 0.5% to about 3% of the composition, and a wetting agent can constitute from about 0.1% to about 5% of the composition.

Dusts can be prepared by mixing the compositions of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to about 60% by weight of the active ingredients are commonly made and are subsequently diluted to about 1% to 10% use concentration.

The compositions of the invention can be applied as sprays by methods commonly employed, such as conventional high-gallonage hydraulic sprays, low gallonage sprays, air-blast spray, aerial sprays and dusts. For low volume applications a solution of the active compounds is usually used. The dilution and rate of application will usually depend upon such factors as the type of equipment employed, the method of application, and the area to be treated.

For some applications, it may be useful to add one or more other insecticides to the compositions of the invention. Examples of other insecticides which can be incorporated to provide additional advantages include parathion, methyl parathion, malathion, carbaryl, methomyl, dicofol, monocrotophos, chlorodimeform, and the like. Other pesticides, including fungicides, viricides, and plant bactericides can also be included in the compositions of the invention.

The following examples will further illustrate this invention but will not intend to limit it in any way. All parts and percentages are by weight unless otherwise indicated.

EXAMPLE 1

This example demonstrates the safening effect of combining toxaphene with O-ethyl S-n-propyl O-2,4,6-trichlorophenyl phosphorothiolate (Compound A) in insecticidal compositions.

Three weeks after planting, cotton plants are sprayed to runoff with a manually held atomizer with formulated insecticidal compositions (prepared from emulsifiable concentrates) containing various rates (lb/100 gal. approximately equal to lb/acre in field applications) of the phosphorothiolate (one part) and toxaphene (five parts). Three days after treatment, the phytotoxicity of the compositions is rated on a scale of 0 (no injury) to 5 (dead plant). Three replicates involving both cotyledonary and true leaves are carried out. The following Table 1 summarizes the results of these tests.

TABLE 1

| | Cotton Phytotoxicity | |
|---|---|---|
| Compound A (lb/100 gal) | Toxaphene (lb/100 gal) | Phytotoxicity |
| (2) | — | 4.3 |
| — | (10) | 0 |
| (2) | (10) | 0.16 |
| (1) | — | 2.7 |
| — | (5) | 0 |
| (1) | (5) | 0 |
| (0.5) | — | 1.7 |
| — | (2.5) | 0 |
| (0.5) | (2.5) | 0 |
| (0.25) | — | 1.5 |
| — | (1.25) | 0 |
| (0.25) | (1.25) | 0 |

EXAMPLE 2

This example shows the safening effect of combining various ratios of toxaphene with O-ethyl S-n-propyl O-2,4,6-trichlorophenyl phosphorothiolate.

Following the procedure of Example 1, three-week old cotton plants are treated with insecticidal compositions containing various weight ratios of O-ethyl S-n-propyl O-2,4,6-trichlorophenyl phosphorothiolate (Compound A). Tables II and IIA summarize the results of these tests.

TABLE II

| | Cotton Phytotoxicity | |
|---|---|---|
| Compound A (lb/100 gal) | Toxaphene (lb/100 gal) | Phytotoxicity |
| 2 | — | 4.8 |
| — | 10 | 0 |
| 2 | 2 | 1.2 |
| 2 | 4 | 0.5 |
| 2 | 8 | 0.17 |
| 2 | 10 | 0.16 |
| 1 | — | 1.7 |
| — | 5 | 0 |
| 1 | 1 | 0.5 |
| 1 | 2 | 0.17 |
| 1 | 4 | 0 |
| 1 | 5 | 0 |

TABLE IIA

| | Cotton Phytotoxicity | |
|---|---|---|
| Compound A (lb/100 gal) | Toxaphene (lb/100 gal) | Phytotoxicity |
| 2 | — | 2.0 |
| — | 1 | 0 |
| 2 | 1 | 1.2 |
| 1 | — | 1.0 |
| — | 0.5 | 0 |
| 1 | 0.5 | 0.7 |
| 0.5 | — | 0.3 |
| — | 0.25 | 0 |
| 1 | 0.25 | 0.2 |
| 0.25 | — | 0 |
| — | 0.13 | 0 |
| 0.25 | 0.13 | 0 |

Higher ratios of Compound A to toxaphene (4:1, 8:1, and the like) can be used to minimize injury by Compound A when such injury is slight to moderate.

EXAMPLE 3

This example shows the effectiveness of toxaphene for safening insecticidal compositions which contain O-ethyl S-n-propyl 4-bromo-2-chlorophenyl phosphorothiolate (Compound B). Following the procedure of Example 1, three-week old cotton plants are treated with compositions containing various concentrations of toxaphene and the phosphorothiolate. These plants are evaluated for phytotoxicity three days after spraying. Phytotoxicity is evaluated on a scale of 0 (no injury) to 5 (dead plant). Table III summarizes the results of these tests.

TABLE III

| | Cotton Phytotoxicity | |
|---|---|---|
| Compound B (lb/100 gal) | Toxaphene (lb/100 gal) | Phytotoxicity |
| 2 | — | 4.0 |
| — | 8 | 0 |
| 2 | 8 | 0.5 |
| 1 | — | 1.8 |
| — | 4 | 0 |
| 1 | 4 | 0.17 |
| 0.5 | — | 1.0 |
| — | 2 | 0 |
| 0.5 | 2 | 0.17 |
| 0.25 | — | 0.7 |
| — | 1 | 0 |
| 0.25 | 1 | 0.17 |

EXAMPLE 4

This example shows the effectiveness of DDT for safening insecticidal compositions which comprise O-ethyl S-n-propyl O-2,4,6-trichlorophenyl phosphorothiolate.

Following the procedure of Example 1, three-week old cotton plants are treated with several levels of insecticidal compositions containing O-ethyl S-n-propyl O-2,4,6-trichlorophenyl phosphorothiolate (Compound A) and DDT in 1:4 and 1:2 weight ratios. Table IV summarizes the results of these tests.

TABLE IV

| | Cotton Phytotoxicity | |
|---|---|---|
| Compound A (lb/100 gal) | DDT (lb/100 gal) | Phytotoxicity |
| 2 | — | 2.8 |
| 1 | — | 1.8 |
| 0.5 | — | 1.0 |
| 0.25 | — | 0.5 |

TABLE IV-continued
Cotton Phytotoxicity

| Compound A (lb/100 gal) | DDT (lb/100 gal) | Phytotoxicity |
| --- | --- | --- |
| — | 8 | 0 |
| — | 4 | 0 |
| — | 2 | 0 |
| — | 1 | 0 |
| — | 0.5 | 0 |
| 2 | 8 | 1.3 |
| 2 | 4 | 1.5 |
| 1 | 4 | 0.8 |
| 1 | 2 | 1.0 |
| 0.5 | 2 | 0.5 |
| 0.5 | 1 | 2.0 |
| 0.25 | 1 | 0.3 |
| 0.25 | 0.5 | 0.2 |

EXAMPLE 5

This example shows the insecticidal activity of the safened compositions of the invention, and demonstrates that these compositions retain the high degree of insecticidal activity possessed by the individual components of the compositions.

Standard initial and one week residual assays are performed on five test species. For initial activity, potten lima bean plants are sprayed to runoff and when dry were infested with $3^d$ instar Mexican bean beetle larvae or southern armyworm larvae. Infested potted lima bean or broccoli plants are similarly sprayed for two-spotted spider mites and green peach aphids respectively. Adult boll weevils contained in screen-capped half-pint mason jars are sprayed on a turntable apparatus. A contact spray on armyworm is included and consists of spraying $3^d$ instar larvae in a petri dish with immediate transfer to an untreated dish containing moist filter paper and a lima bean leaf.

Residual assays consist of spraying the appropriate plants and jars as above, infesting same seven days after the date of application. Exposure periods as as follows:
  worm: initial and residual 72 hours, contact 48 hours
  beetle: initial and residual 72 hours
  boll weevil: initial and residual 48 hours
  aphid and mite: initial 24 hours, residual 48 hours Table V summarizes the results of these tests. The $LC_{50}$ values are based on parts per million of active ingredient.

TABLE V

| Insecticidal Activity ($LC_{50}$-ppm) | | | | | | |
| --- | --- | --- | --- | --- | --- | --- |
| INITIAL KILL | | | | | | |
| | armyworm Stomach | armyworm contact | Mexican bean beetle | 2-spot spider mite | green peach aphid | boll weevil |
| Compound A | 13 | 20 | 3.8 | 0.19 | 2.1 | 42 |
| Toxaphene | 26 | >75 | 98 | >300 | 68 | >600 |
| Compound A + Toxaphene(1:2)* | 10.8 | 105 | 6 | 1.2 | 6 | 225 |
| 7 DAY RESIDUAL | | | | | | |
| | armyworm | | Mexican bean beetle | 2-spot spider mite | green peach aphid | boll weevil |
| Compound A | 300 | | 500 | 600 | 1325 | 163 |
| Toxaphene | 420 | | 490 | >1200 | >2400 | >1200 |
| Compound A + Toxaphene(1:2)* | 250 | | 525 | 900 | 2130 | 225 |

*$LC_{50}$ based on total active ingredient (phosphorothiolate plus toxaphene)

It is to be understood that changes and variations may be made without departing from the spirit and scope of the invention as defined by the appended claims.

We claim:

1. A method of controlling insects in cotton which comprises applying to the growing cotton an insecticidal composition which comprises a phosphorothiolate of the formula

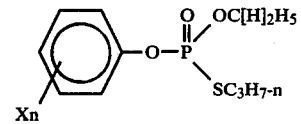

wherein
X is a halogen atom, and
n is 1, 2, or 3,
and, as a safening agent, toxaphene or DDT or a mixture of toxaphene and DDT in an amount effective to reduce the phytotoxicity of the composition to cotton wherein the composition is applied at a rate of about 0.5 to about 12 pounds of total phosphorothiolate plus safening agent per acre and the weight ratio of the phosphorothiolate to the safening agent is about 1:1 to about 1:5.

2. The method of claim 1 wherein the safening agent is toxaphene.

3. The method of claim 2 wherein the phosphorothiolate is O-ethyl S-n-propyl O-2,4,6-trichlorophenyl phosphorothiolate.

4. The method of claim 2 wherein the phosphorothiolate is O-ethyl S-n-propyl O-4-bromo-2-chlorophenyl phosphorothiolate.

5. The method of claim 1 wherein the weight ratio of the phosphorothiolate to the safening agent is about 1:2 to about 1:5 and the safening agent is DDT.

6. The method of claim 5 wherein the phosphorothiolate is O-ethyl S-n-propyl O-2,4,6-trichlorophenyl phosphorothiolate.

* * * * *

UNITED STATES PATENT AND TRADEMARK OFFICE
CERTIFICATE OF CORRECTION

PATENT NO. : 4,251,523

DATED : February 17, 1981

INVENTOR(S) : Harold E. Aller and Carl O. Hansen

It is certified that error appears in the above-identified patent and that said Letters Patent are hereby corrected as shown below:

Please amend the formula in claim 1 to read as follows:

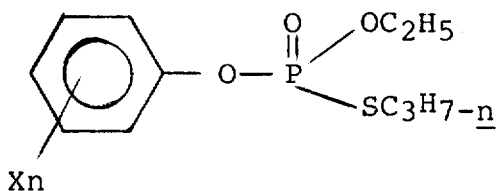

Signed and Sealed this

Ninth Day of June 1981

[SEAL]

Attest:

RENE D. TEGTMEYER

Attesting Officer

Acting Commissioner of Patents and Trademarks